United States Patent [19]
Breimesser et al.

[11] Patent Number: 4,589,284
[45] Date of Patent: May 20, 1986

[54] ULTRASONIC TOMOGRAPHY UNIT

[75] Inventors: Fritz Breimesser, Erlangen; Dietrich Hassler, Uttenreuth; Eckart Hundt, Haar; Gerd Maderlechner, Groebenzell; Elmar Trautenberg, Fuerth, all of Fed. Rep. of Germany

[73] Assignee: Siemens Aktiengesellschaft, Berlin and Munich, Fed. Rep. of Germany

[21] Appl. No.: 683,304

[22] Filed: Dec. 17, 1984

[30] Foreign Application Priority Data

Dec. 27, 1983 [DE] Fed. Rep. of Germany ....... 3347200

[51] Int. Cl.⁴ ............................................. G01N 29/04
[52] U.S. Cl. ..................................................... 73/626
[58] Field of Search ........................ 73/626, 625, 620; 128/660; 367/103, 105

[56] References Cited

U.S. PATENT DOCUMENTS

| 4,279,157 | 7/1981 | Schomberg et al. | 73/626 |
| 4,398,422 | 8/1983 | Haerten | 73/626 |
| 4,478,083 | 10/1984 | Hassler et al. | 73/620 |

Primary Examiner—Stephen A. Kreitman
Attorney, Agent, or Firm—Mark H. Jay

[57] ABSTRACT

An ultrasonic head is a linear array consisting of a plurality of transducer elements. The array is perpendicular to a sectional plane of the object under study and can be rotated about its longitudinal axis. Several groups each consisting of jointly controlled transducer elements are driven to form a beam aperture. Between each two adjacent driven groups there is provided at least one group that is switched off. The ultrasonic tomography unit thus obtained scans several parallel section levels one after the other or even, at least approximately simultaneously, without additional mechanical movement.

2 Claims, 2 Drawing Figures

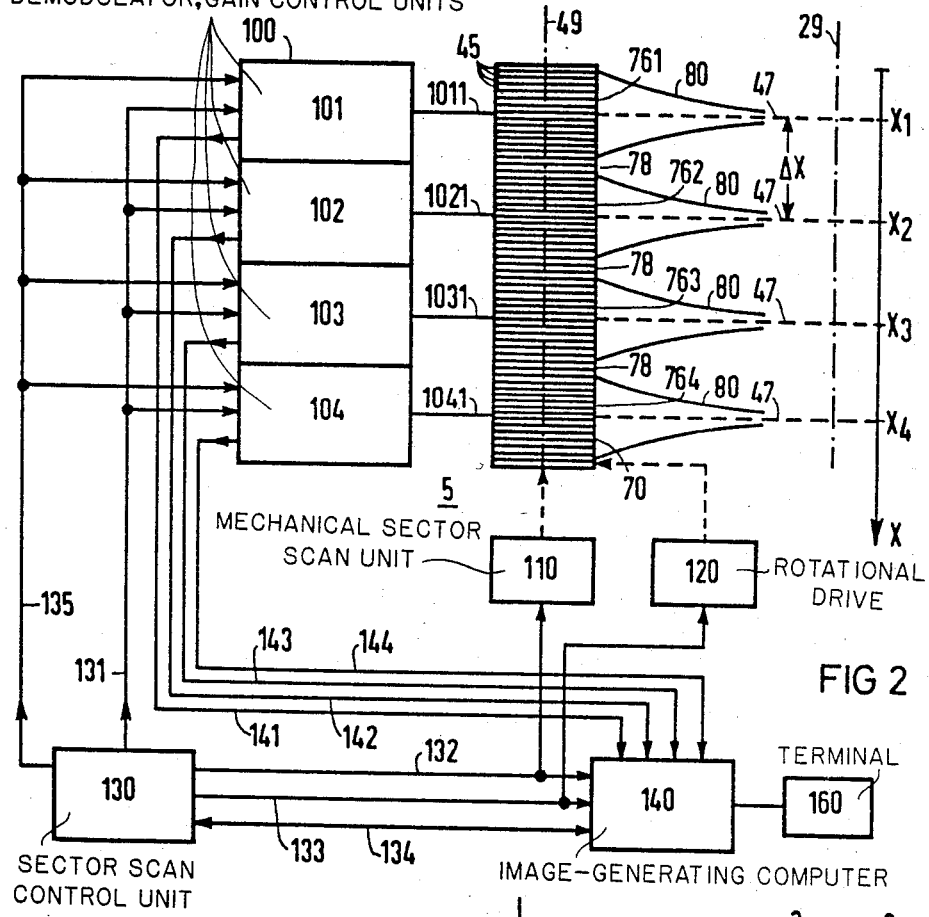
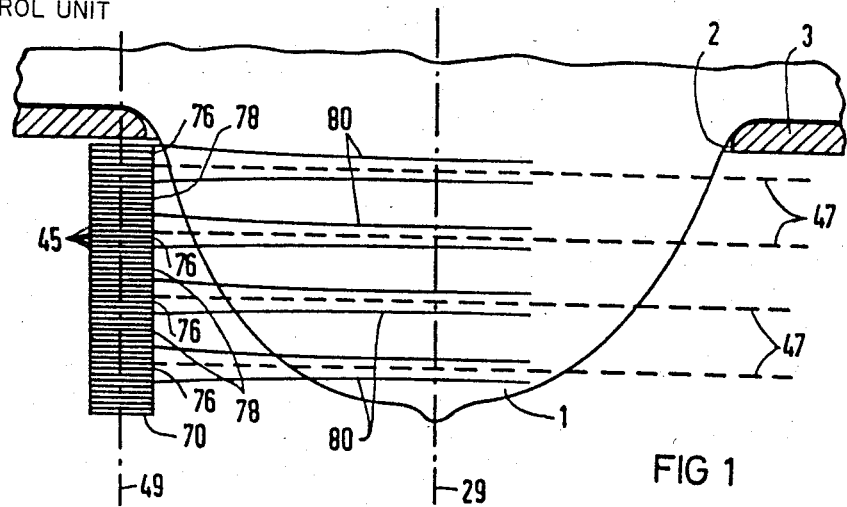

ULTRASONIC TOMOGRAPHY UNIT

BACKGROUND OF THE INVENTION

U.S. Pat. No. 4,478,083 relates to an ultrasonic tomography unit with an ultrasonic sending/receiving system designed for line-by-line scanning from a number of angular directions of an object under study. The ultrasonic sending/receiving system includes ultrasonic heads, individually or in groups, which scan the object under study line-by-line from various angular directions and which can be focused in corona or corona-like scanning levels at various object depths, and to which are assigned an adjustment device for adjusting the tilt angle of the respective sending/receiving beam, as well as a time gate circuit to permit signal data from the various object depths in the focus ranges to be received in sections.

The groups of ultrasonic heads can be designed in different ways. For example, the ultrasonic heads can include transducer elements, which, for example, can be set up as a linear array, an array for electronically controlled sector scanning, or as a ring array. However, the ultrasonic head can also include an individual ultrasonic transducer, which might be a component of a slowly rotating sector scanner. In addition, the ultrasonic heads can also be arranged at intervals on the circumference of a rotating disk. The disk rotates (together with the mechanical sector scanners) around the axis passing through the object to be investigated. To generate the sector scanning fields, the sector scanners may have a simple swivel motion. In addition, the individual sector scanners may also be scanners that rotate through a full circle. In both cases the frequency of rotation of the disk is much lower than the frequency with which the sector scanner is swiveled or rotated. Thus, for example, the rotational speed of the annular disk together with the sector scanner might be about 0.1 Hz. The swiveling or rotational frequency of the sector scanner, on the other hand, is about 3 or 4 Hz. An ultrasonic array may also be used as an ultrasonic head. This ultrasonic array can, for example be a linear array or an array with an electronically controlled beam sweep for sector scanning, which is likewise rotated slowly along an arc about the axis passing through the object to be investigated. The linear array is preferably a multi-line array in which the individual transducer elements are arranged in a matrix. A variety of apertures can be obtained for sending and/or receiving, using the conventional practice of electronic connection or disconnection of individual elements, thereby forming beam groups of various sizes. In addition to a linear array, which scans the object under study in a linear manner, a ring array is also provided, in which case the beam sweep and its step-by-step progression along the ring array takes place by purely electronic means.

One purpose of the invention, then, is to improve an ultrasonic tomography unit of the kind described above. Another object is to scan several parallel section planes one after the other or even approximately simultaneously, without additional mechanical movement.

In accordance with the invention, the ultrasonic head is a linear array, which consists of a plurality (preferably several hundred) linearly arranged transducer elements. This array is perpendicular to a section plane of the object under study, and can also be rotated about its longitudinal axis. Several groups, each consisting of jointly controlled transducer elements, form in each case a beam aperture. These beam apertures, each of which consists of a plurality (advantageously at least 15 and preferably 30) of linearly arranged transducer elements, are simultaneously stepped by electronic means, for example, according to a group stepping system, advantageously according to a half-step process and preferrably according to a modified half-step process. Between every two adjacent driven groups there is provided at least one group that is switched off. By designing the ultrasonic tomography unit in this manner, it is possible to scan several parallel section planes at least approximately simultaneously.

BRIEF DESCRIPTION OF THE DRAWING

An exemplary and non-limiting preferred embodiment of the invention is shown in the drawings, in which:

FIG. 1 schematically illustrates a preferred embodiment of the invention; and

FIG. 2 is a block diagram of the electronic control system for the preferred embodiment.

DETAILED DESCRIPTION OF PREFERRED EMBODIMENTS

A female breast, as the object 1 under study, projects through an application opening 2 in a plate 3, which is an element of a table on which the patient lies. An ultrasonic sending/receiving system 5 (FIG. 2) contains an ultrasonic head 70 and scans the object 1 line-by-line from various angles. In addition, the ultrasonic sending-/receiving system 5 is equipped with a rotational drive 120 (FIG. 2) for rotation about an axis 29. The ultrasonic head 70 is formed by a linear array consisting of a plurality of transducer elements 45, the array being arranged perpendicular to a section plane 47 of the object 1. In addition, the linear array is also mounted so that it can be rotated about its longitudinal axis 49. Several groups 76 each contain a plurality (advantageously at least 15 and prefeably 30) of transducer elements 45 that are linearly arranged and form, in each case a beam aperture. Furthermore, between each two adjacent driven groups 76, there is provided at least one group 78 that is switched off, so that the individual radiation pressure fields 80 of the driven groups 76 do not interfere with one another. These individually driven groups 76 are in each case provided, through an electronic step-by-step progression system, with an electronic focussing and parallel scanning of the sonic field. In addition, it is also possible to electronically swivel the ultrasonic beam of the driven group 76.

FIG. 2 illustrates the control electronics for the ultrasonic sending/receiving system 5. The sending and receiving electronics unit 100 is constituted by a plurality (here, four) of like units 101 through 104, which are connected with the ultrasound head 70 and which control a like plurality (here four) of groups 761 through 764 of ultrasound transducer elements 45. The units 101 through 104 each contain a transmitter, a time-gain-control receiver, a demodulator, and a scan control unit, which moves the section plane 47 in the scan direction X. The ultrasonic sending/receiving system 5 can be rotated about the axis 49 by means of a mechanical sector scan unit 110, and can be rotated about the axis 29 by means of a rotational drive 120. The initiating control pulse is sent by sector scan control unit 130 along control lines 132 and 133. The scan control unit 130 also provides control signals on line 131 for units 101 through 104, which latter provide sending impulses over lines 1011 through 1041 to the ultrasound head 70. The returning echo information is conducted to an analog-to-digital converter of an image-generating computer 140 over lines 141 to 144 and is stored there. The scan control unit 130 also provides position information particularly for the actual angular position of the array 70 with respect to axis 49 and 29 via lines 132 and 133, and also sends information relating to the height of the scan in the X direction over line 134 to computer 140. Approximately 200 to 300 microseconds after the first sending impulse is sent along line 132 by a control impulse, the array is rotated a predetermined angular step around the axis 49. Thereafter, the accumulation of A-scan information is initiated once again over the control line 131. At a fixed angular position about the axis 29 and a fixed height $X_1$ through $X_4$, a B-scan picture about the axis 49 is generated step-by-step. Afterwards, a control impulse is provided to the rotational drive 120 over line 133. This causes a rotation of the ultrasonic sending/receiving system 5 in a predetermined angular amount about the axis 29. Afterwards, a new B-scan picture at this new angular position about the axis 29 is constructed about the axis 49. The totality of all A-scan information, which is generated at varying angular positions about the axes 49 and 29 at a constant height position $X_1$ to $X_4$, is assembled into a CT-picture by the computer 140 and displayed on a terminal 160. Thereafter, the scan control unit 130 generates a control pulse over line 135 to the units 101 through 104 to advance the array scan one step in the X direction. The maximal scan width $\Delta X$ represents the distance between adjacent section planes 47.

By these means an ultrasonic tomography device is obtained that, on the one hand, produces corona-like sectional pictures close to the breast wall without any excessive technical effort, and, on the other, scans several parallel section planes 47 of the object 1, at least approximately simultaneously.

Under certain circumstances it is advisable to provide a ring array, in which each of several groups 76, each consisting of jointly controlled transducer elements 45, form a beam aperture. In this embodiment, there is also at least one switched-off group 78 between each two adjacent driven groups 76. By this means an ultrasonic tomography unit is obtained that produces corona-like pictures near the breast wall or scans other parallel section planes 47 of the object 1, at least approximately simultaneously, without the need to mechanically move away the ultrasonic sending/receiving system 5.

Those skilled in the art will understand that changes can be made in the preferred embodiments here described, and that these embodiments can be used for other purposes. Such changes and uses are within the scope of the invention, which is limited only by the claims which follow.

What is claimed is:

1. An ultrasonic head for use in ultrasonic tomography units for scanning an object line by line from a plurality of angles using a rotational drive which rotates the head about an axis, comprising:
   a linear array of ultrasonic transducer elements, the array being perpendicular to a section plane of the object and being rotatable about its axis; and
   means for controlling the transducer elements in groups such that a plurality of groups are controlled in such a manner as to simulate simultaneous control thereof, selected groups each form by coaction a beam aperature and adjacent ones of said selected groups are separated from each other by a group of unenergized transducer elements, and ultrasonic beams produced by the groups are non-overlapping.

2. The ultrasonic head of claim 1, wherein said means is a step-by-step progression system which comprises means for electronically focussing and parallel scanning of an ultrasonic beam.

* * * * *